United States Patent
Kergosien et al.

(10) Patent No.: US 9,925,396 B2
(45) Date of Patent: Mar. 27, 2018

(54) ADHESIVE ARTICLE CONTAINING COLORANT AND/OR ACTIVE AGENT

(75) Inventors: Guillaume Kergosien, Chaville (FR); William Meathrel, York, PA (US)

(73) Assignee: L'OREAL, Paris (FR)

( * ) Notice: Subject to any disclaimer, the term of this patent is extended or adjusted under 35 U.S.C. 154(b) by 643 days.

(21) Appl. No.: 12/863,893

(22) PCT Filed: Jan. 30, 2009

(86) PCT No.: PCT/US2009/032624
§ 371 (c)(1),
(2), (4) Date: Nov. 9, 2010

(87) PCT Pub. No.: WO2009/097517
PCT Pub. Date: Aug. 6, 2009

(65) Prior Publication Data
US 2011/0117174 A1 May 19, 2011

Related U.S. Application Data

(60) Provisional application No. 61/024,721, filed on Jan. 30, 2008.

(51) Int. Cl.
*A61F 13/10* (2006.01)
*A61Q 3/02* (2006.01)
*A61K 8/73* (2006.01)
*A61K 8/81* (2006.01)
*A61K 8/85* (2006.01)

(52) U.S. Cl.
CPC ............... *A61Q 3/02* (2013.01); *A61K 8/731* (2013.01); *A61K 8/8147* (2013.01); *A61K 8/85* (2013.01); *A61K 2800/88* (2013.01); *A61K 2800/884* (2013.01)

(58) Field of Classification Search
None
See application file for complete search history.

(56) References Cited

U.S. PATENT DOCUMENTS

| 4,745,934 A * | 5/1988 | Mast et al. ............... 132/73 |
| 5,977,217 A * | 11/1999 | Socci et al. .............. 524/35 |
| 2005/0163732 A1 | 7/2005 | Ramin et al. |
| 2005/0255061 A1 * | 11/2005 | Park ........................ 424/61 |
| 2007/0009454 A1 | 1/2007 | Thevenet |

FOREIGN PATENT DOCUMENTS

| EP | 1 411 069 | 4/2004 |
| WO | WO 04/028488 | 4/2004 |
| WO | 2007 039832 | 4/2007 |

OTHER PUBLICATIONS

Eastman, Cellulose Acetate Butyrate (CAB-381-20), (Jan. 31, 2001), pp. 1-3.*
Office Action dated Jul. 3, 2013, in Chinese Patent Application No. 200980104310.5.
Office Action dated Jan. 23, 2014 in Chinese Patent Application No. 200980104310.5.
Chinese Reexamination Notice dated Aug. 21, 2014 in Chinese Patent Application No. 200980104310.5 (with English language translation).
Chinese Reexamination Decision dated Jan. 21, 2015, in Chinese Patent Application No. 200980104310.5 (w/ English Language Translation).

* cited by examiner

*Primary Examiner* — Dennis J Parad
*Assistant Examiner* — Lyndsey Beckhardt
(74) *Attorney, Agent, or Firm* — Oblon, McClelland, Maier & Neustadt, L.L.P.

(57) ABSTRACT

The invention relates to adhesive articles containing at least one colorant and/or at least one active agent as well as to methods of using such articles on mucosis or keratin materials to achieve a desired result or benefit and to methods of making such adhesive articles.

20 Claims, 2 Drawing Sheets

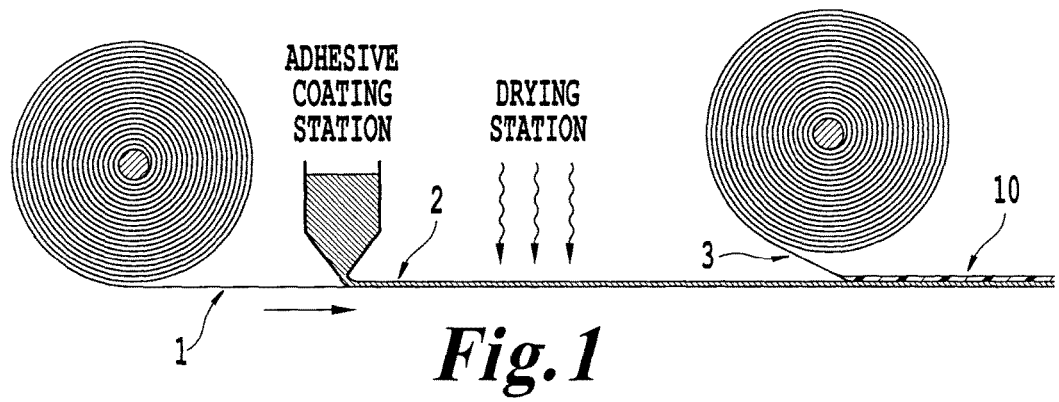
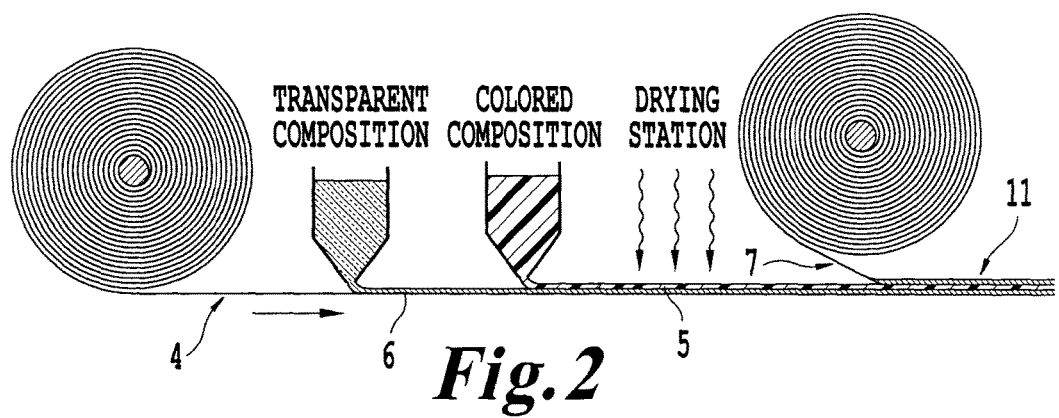
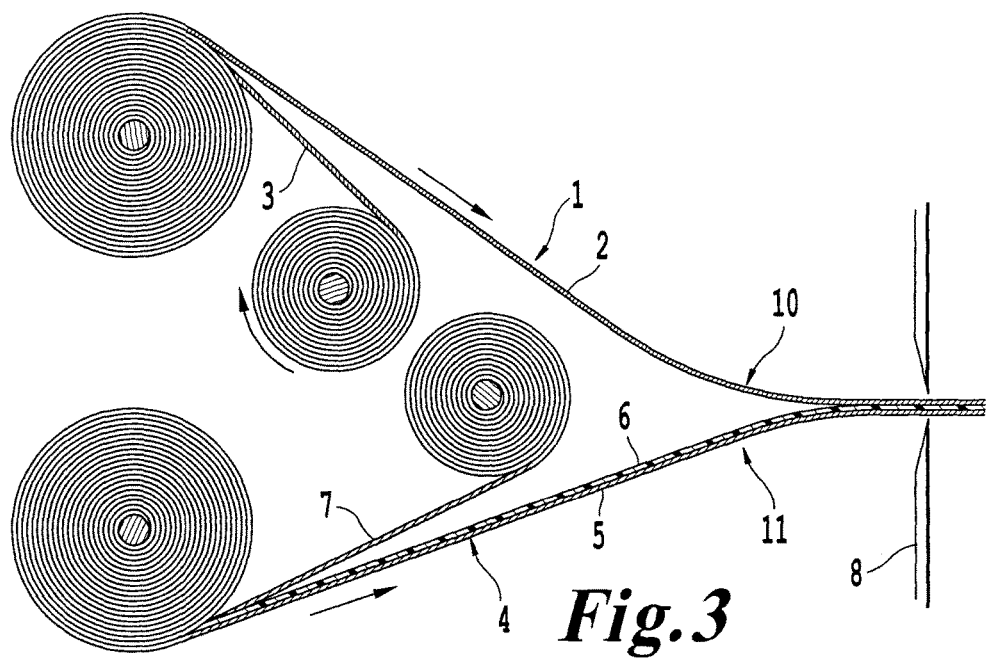

ADHESIVE ARTICLE CONTAINING COLORANT AND/OR ACTIVE AGENT

CROSS REFERENCE TO RELATED APPLICATIONS

This application claims priority to U.S. provisional application No. 61/024,721, filed Jan. 30, 2008, the disclosure of which is hereby incorporated by reference.

FIELD OF THE INVENTION

The present invention generally relates to adhesive articles for use on mucosis or keratin materials as well as to methods of using such articles on mucosis or keratin materials to achieve a desired result or benefit, and to methods of making such adhesive articles. Such articles can be used, for example, for makeup, skin care or oral care purposes. Other potential applications for the article include a temporary cover for injured, broken or torn nails, a camouflaging cover for skin blemishes such as age spots, acne or scars, a releasing device for active agents such as fragrances or pharmaceutically active agents, and a temporary tattoo.

BACKGROUND OF THE INVENTION

Applying color to finger nails is generally time consuming, requiring application of several layers of nail varnish, each of which must be allowed to dry. Despite this cumbersome application process, after only 3 to 5 days, the varnish can flake away and the gloss of the varnish diminishes causing the user to remove the varnish and start the process over again.

Furthermore, when nail varnish is colored, its application is difficult and time-consuming because the user generally attempts to avoid spreading the varnish onto the nail contour—retouching the nail using a solvent is difficult because it dissolves the varnished areas of the nails where varnish has been appropriately applied in addition to the areas where the varnish has spread.

Thus, different ways to apply decorative materials to fingernails and other keratin materials are sought after.

U.S. Pat. No. 4,903,840 relates to an adhesively-securable fingernail covering product. The nail polish-like material is provided in semi-solid form on a sheet of adhesive-backed peel-off paper which, when removed, exposes the adhesive of the fingernail coatings. The fingernail coatings are, after removal from an air-tight package, cut into individual sections, located on the fingernails and pressed onto the fingernails to secure them there, temporarily, i.e., until they are desirably removed. The semi-solid nail enamel product is originally sealed in an air tight envelope to ensure that the coatings do not fully dry out during shipping and storage. The use of this air tight envelope is restricting, and cannot be avoided since the product still contains solvent. After a short period of time out of the tight packaging, the article becomes difficult to apply since it does not stretch easily and tends to break when applied to a curved surface.

U.S. Patent Application 2005/255061 provides examples of film formulas usable in a nail appliqué. Some examples suffer from the same drawbacks discussed above with respect to U.S. Pat. No. 4,903,840. Other examples have poor abrasion resistance which leads to poor wear characteristics.

U.S. Pat. No. 5,415,903 from LTS Lohman Therapie-Systeme GmbH & Co. KG generally relates to a self-adhesive laminate, shapeable to toe and fingernails, containing a) a film-forming polymer layer containing at least one plasticizer, b) a pressure-sensitive adhesive layer located thereon, and c) a removable carrier film which covers the pressure-sensitive adhesive layer, wherein the film-forming layer a) is also covered on the other side with d) a protective layer, which is likewise removable and is resistant to the other constituents of the laminate and the materials used in the preparation of the laminate. The examples do not lead to laminates having sufficient stretchability—generally speaking, when laminates are applied on curved nails, it is necessary/desirable that the laminates can be stretched (have sufficient stretchability) to avoid wrinkles on nails' sides.

French Patent 2870452 from L'Oreal relates to a flexible article with optical-, render- and/or olfactory-effect for make-up, nail care and/or nails comprising an adhesive layer for fixing on the nail, an organic film and a material with optical, rendering and/or olfactory effect.

French Patent 2870453/WO2005112874 from L'Oreal relates to a flexible article which is used to make up and/or care for nails and/or false nails, comprising: at least one adhesive layer which is used to fix the article to the nail, and at least one cross-linked film.

French Patent 2870454 from L'Oreal relates to a flexible article for make-up, nail care and/or false nail care comprises an adhesive layer, and a polymeric film obtained by evaporation of aqueous phase of an aqueous dispersion of particles of at least a film-forming polymer.

PCT Patent Application WO2007/039832 from L'Oreal relates to a method for make-up and/or care of the nails comprising gluing onto the nail, by means of an adhesive, a flexible sheet comprising at least one layer of at least one organic and/or inorganic material, the organic or inorganic material and/or the adhesive containing at least one silicone compound, said sheet having a thickness in the range from 1 µm to 2 mm.

Nevertheless, there remains a need for improved adhesive articles which are long-lasting and/or which can be applied quickly and easily.

Accordingly, one aspect of the present invention is a care and/or makeup and/or treatment article for mucosis or keratin materials which has such properties and/or is able to address or overcome the aforementioned problems with the prior art compositions.

BRIEF SUMMARY OF THE INVENTION

The present invention relates to an adhesive article comprising colorant and/or active agent for use on mucosis or keratin materials.

The present invention further relates to an adhesive article comprising colorant and/or active agent comprising an adhesive layer and a polymeric layer. Such an adhesive article may further comprise a protective or removable layer on one or both sides of the article, The present invention further relates to an adhesive article comprising colorant and/or active agent comprising an adhesive layer and a polymeric layer, wherein the polymeric layer has a Persoz hardness less than 50 seconds, preferably less than 40 seconds, more preferably less than 35 seconds, and most preferably less than 30 seconds, and a resistance to abrasion corresponding to a weight loss lower than 50 mg, preferably lower than 40 mg, more preferably lower than 30 mg, and most preferably lower than 20 mg, the polymeric arrangement being configured so that, when the article is also substantially free of solvent, the elongation at break of the article is greater than 30%, preferably greater than 40%, more preferably greater than 50%, and most preferably greater than 60%.

The present invention further relates to methods of applying an adhesive article comprising colorant and/or active agent to mucosis or a keratin material.

The present invention also relates to methods of treating, caring for, making up or enhancing the appearance of mucosis or keratin materials comprising applying adhesive articles of the present invention to the mucosis or keratin materials to treat, care for, make-up and/or enhance the appearance of the keratin materials.

The present invention further relates to methods of making an adhesive article comprising an adhesive layer and a functional or polymeric layer comprising at least one colorant and/or at least active agent, comprising: contacting a first laminate comprising the adhesive layer with a second laminate comprising the functional or polymeric layer to form a sheet comprising the adhesive layer and the functional or polymeric layer. Preferably, the adhesive layer is adjacent to and in contact with the functional or polymeric layer. Then, the sheet can be cut into an appropriate size and shape to form the decorative and/or care adhesive article.

The present invention also relates to methods of making an adhesive article comprising preparing a first laminate by coating an adhesive layer onto a first substrate, preparing a second laminate by coating a polymeric or functional layer onto a second substrate, and contacting the first laminate with the second laminate to form an adhesive article. Such processes can also include exposing the first laminate to elevated temperatures to remove solvent and/or cross-link materials present in the adhesive layer. Such processes can further include cutting the adhesive articles into various sizes and shapes for easy application to mucosis or keratin materials such as nails.

It is to be understood that both the foregoing general description and the following detailed description are exemplary and explanatory only, and are not restrictive of the invention.

BRIEF DESCRIPTION OF THE DRAWINGS

FIG. 1 depicts a cross-sectional view of the production of a first laminate formed by coating an adhesive layer onto a substate.

FIG. 2 depicts a cross-sectional view of the production of a second laminate formed by coating a polymeric layer onto a substrate.

FIG. 3 depicts a cross-sectional view of the production of an adhesive article by contacting the first and second laminates of the preceding figures.

DETAILED DESCRIPTION OF THE INVENTION

Figure 4:
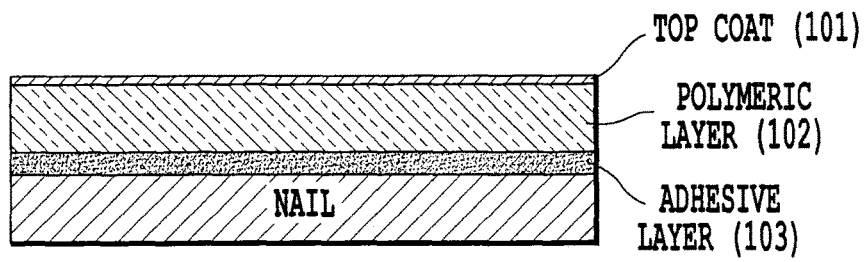
FIG. 4 depicts a cross-sectional view of an example of a decorative article in accordance with the present invention as prepared in Examples 1 and 2.

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Cosmetically acceptable" means that the item in question is compatible with any keratin material. For example, "cosmetically acceptable medium" means a medium that is compatible with any keratin material.

"Keratin material" includes, for example, skin, hair, nails, eyelashes, eyelids, eyebrows, lips and any other area of body or facial skin. "Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Volatile", as used herein, means having a flash point of less than about 100° C.

"Non-volatile", as used herein, means having a flash point of greater than about 100° C.

"Water-insoluble," as used herein, means that the reaction product retains its structure and does not solubilize upon exposure to water.

The compositions, methods and kits of the present invention can comprise, consist of, or consist essentially of the essential elements and limitations of the invention described herein, as well as any additional or optional ingredients, components, or limitations described herein or any otherwise useful ingredient found in personal care compositions intended for application to keratin materials.

"Persoz hardness" can be determined by any suitable means within the art. For example, Persoz Hardness can be determined using a Persoz Pendulus at a defined temperature (for example, 30° C.) at a defined humidity (for example, 50% RH). A suitable protocol is set forth below:

Any protective layer or release liner is removed from the specimen. The adhesive side of the specimen is applied to the glass plate, and then the specimen is dried at 30° C. for 23 hours, and for 1 additional hour in the pendulous environment.

The Persoz pendulus is then positioned on the specimen which is applied on the glass plate. The time it takes the Persoz pendulous to oscillate from amplitude of 12° to amplitude of 4° is then determined for numerous runs (for example, 10 measurements), and then the average is calculated.

"Abrasion resistance" can be determined by any suitable means within the art. For example, specimens can be subjected to the action of abrasive wheels at a defined force, and their resistance to such abrasion can be determined.

For example, a "5130 ABRASER" available at "TABER INDUSTRIES" can be used. Such an abrasimeter is typically composed of:

a) A table turning at a speed of (60+/−2) turns/min allowing the sample to be fixed;

b) Two abrasive wheels (for example, Taber CS-10F) with side mass of 250 g per wheel.

c) A disc having an external diameter of 100 mm.

d) A device carrying the disc e) A revolution counter to determine the number of revolutions of the rotary table, and f) A suction device.

The abrasimeter is run at a defined temperature (for example, 23° C.) and at a defined humidity (for example, 26% RH).

A suitable protocol is set forth below.

First, clean the disc with a suitable solvent such as acetone. Next, prepare multiple samples to undergo abrasion resistance testing, (for example, eight samples). Suitable samples for wheels of a size identified above are 10 mm×20 mm. Remove any protective layer or release liner from the samples to be tested. The samples are applied to the disc using their adhesive sides so that the samples are perpendicular to the movement of the wheel and equally spaced from each other (see, FIG. 4). The disc with the samples on it is dried for 24 hours at 30° C. Measure the weight of the disc with the samples on it to determine the pre-abrasion weight.

Before taking any measurements, resurface the wheel by turning it multiple times (for example, 20 times). Then, program the abrasimeter for the desired number of revolutions, and run the device. After the revolutions, measure the weight of the disc with the samples on it, and determine weight loss.

"Tensile strength" can be determined by any suitable means within the art. In theory, the test evaluates the mechanical properties of the specimens by stretching them until they break. The test determines elongation at break, the elastic modulus, the rupture stress and the rupture energy. A suitable protocol is set forth below.

Figure 5:
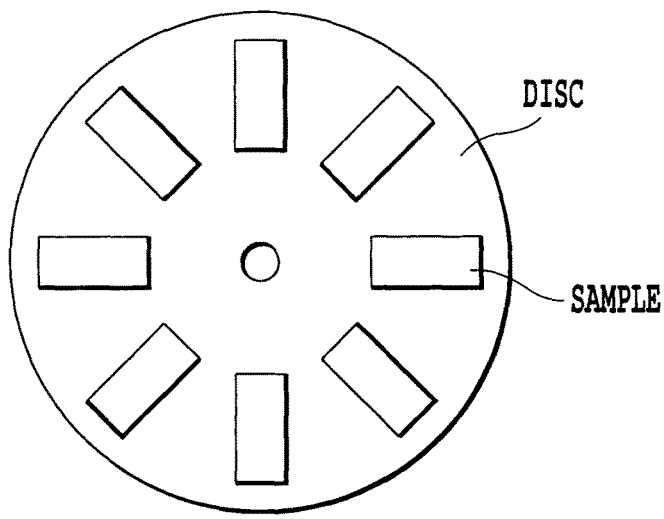
FIG. 5 a cross-sectional view of an example of samples which are applied to a disc so that the samples are perpendicular to the movement of the wheel and equally spaced from each other useful for determining abrasion resistance.
Figure 6:
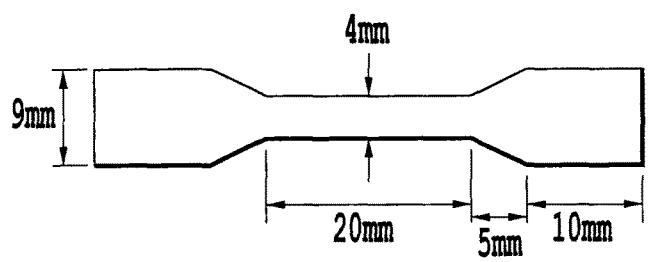
FIG. 6 depicts a cross-sectional view of an example of a bow-tie shaped sample useful in determining tensile strength.

Remove any protective layer or release liner from the samples to be tested, and dry the samples at 30° C. for 24 hours. Cut the samples to be tested (for example, six samples) in a bow-tie shape (see, FIG. 5 for a specific example of such a shape).

Prepare a tensile testing machine (for example, a texture analyser TA-XT2i used in traction mode) in a standard environment including a defined temperature and a defined relative humidity (for example, 19° C. and 30% RH). Set the machine for an appropriate traction speed (for example, 50 mm/min). Mount the specimen in the clamps so that the narrow, central part of the specimen is between the clamps of the machine, and run the machine. The result should be a curve depicting stress (MPa) versus strain (%). From this, the average elongation at break for all specimens tested can be determined.

"Tack" or "work of debonding" can be determined by any suitable means within the art. An example of a suitable protocol is set forth below.

First, prepare the sample to be tested. The sample surface has to be greater than 5 mm×5 mm.

Prepare a tack testing machine (for example, a texture analyser TA-XT2i) to evaluate the work of debonding on the sample. Install the tack probe. The tack probe can be a stainless steal cylinder with a diameter of 5 mm. The reference of this tack probe can be "SMS P/5". Next, any protective layer or release liner should be removed from the sample, and the sample should be dried at 30° C. for 24 hours. Then, apply a double sided adhesive tape on a plate at 35° C., and then apply the sample to be evaluated on the adhesive tape, so that the non adhesive side of the sample is in contact with the adhesive tape.

In running the device, the speed before compression can be 0.1 mm/s. The compression force (compression step) can be 0.01 MPa (for 20 seconds). Speed after compression (traction step) can be 0.1 mm/s. The work of debonding during the traction step is evaluated. The value corresponds to the area under the curve corresponding to pressure as a function of displacement during the traction step ($J/m^2$). The device can be run in a standard environment including a defined temperature and a defined relative humidity (for example, 19° C. and 30% RH).

"Thermal Resistance" can be determined by any suitable means within the art. An example of a suitable protocol is set forth below.

First, remove any protective layer or release liner from the sample, and prepare a sample to be tested by drying the specimen in a standard environment (for example, dry at 25° C. at 50% RH for 24 hours).

Prepare a thermal resistance testing machine (for example, a TGA 209C from Netzsch) according to the following conditions.

Purge gas: Air (flow=30 ml/min)

Crucible: Platinum cupel 50 µl from TA Instruments.

Temperature calibration: Curie point of Alumel, Nickel, Perkaloy and iron.

Weight calibration: Standard weight of 1 g

Sample weight: 3 to 7 mg

Thermal treatment: Heating from 30° C. to 400° C. at 5° C./min.

Adhesive Layer

According to the present invention, adhesive articles comprising an adhesive layer are provided. In accordance with the present invention, any suitable adhesive material can be used in the adhesive layer. Preferably, the adhesive material is a pressure sensitive adhesive, and the pressure sensitive adhesive is a medical or pharmaceutical grade adhesive that is suitable for cosmetic applications in that it is non-cytotoxic, non-sensitizing and non-irritating.

For the purposes of the present invention, the term "adhesive material" means a polymer or a polymeric system having adhesive properties that may comprise one or more polymers, possibly of different nature. This adhesive material may be in the form of a polymer solution or a dispersion of polymer particles in a solvent. This adhesive material may also contain a film modifying agent such as a plasticizer. As known in the art, depending on the nature of the adhesive material, it may be necessary to expose the material a radiation source such as, for example, electron beam, gamma radiation, ultra violet radiation or thermal energy, to convert the material into a pressure sensitive adhesive.

According to the present invention, the adhesive material may be chosen from adhesives of "Pressure Sensitive Adhesives" type, for instance those cited in the "Handbook of Pressure Sensitive Adhesive Technology" 3rd edition, D. Satas, the disclosure of which is hereby incorporated by reference.

According to preferred embodiments, the adhesive material may be coated from an aqueous or organic solvent directly onto a substrate such as a protective or removable layer. According to such embodiments, the solvent is preferably removed from the adhesive layer prior to forming the adhesive article by forming or combining a polymeric or functional layer on or with the adhesive layer.

According to other preferred embodiments, the adhesive material does not contain effective amounts of solvent (that is, it is essentially free of solvents or completely free of solvents). According to such embodiments, the adhesive layer can be directly formed on either a substrate such as a protective layer or removable layer or on a polymeric layer.

According to the present invention, suitable solvent-based pressure sensitive adhesives include polymeric resins dissolved or dispersed in a solvent. The chemical composition of the polymeric resin may be based on acrylic polymers, natural and synthetic rubbers, silicone polymers and hybrid compounds that combine acrylic and rubber components or acrylic and silicone based polymers. Plasticizers, tackifiers, surfactants, cross-inking compounds may be included in the adhesive formulation to control the physical properties of the dried and cured adhesive layer as is known in the art.

Suitable adhesive materials include polymers chosen from block or statistical copolymers comprising at least one monomer or a combination of monomers whose resulting polymer has a glass transition temperature of less than room temperature (25° C.), these monomers or associations of monomers possibly being chosen for example from butadiene, ethylene, propylene, isoprene, isobutylene and a silicone, and mixtures thereof. Specific examples of such suitable materials include, but are not limited to, block polymers of styrene-butadiene-styrene, styrene-(ethylene-butylene)-styrene or styrene-isoprene-styrene type, for instance those sold under the trade names "Kraton®" from SHELL CHEMICAL Co. or "Vector®" from EXXON, polyurethanes, acrylic polymers, silicones, butyl rubbers, ethylene-vinyl acetate polymers, polyamides optionally modified with fatty chains, natural rubbers, and mixtures thereof. They may in particular be adhesive copolymers derived from the copolymerization of vinyl monomers with polymeric species, for instance those described in patent U.S. Pat. No. 6,136,296, or those polymers described in U.S. Pat. No. 5,929,173, having a polymer backbone, with a Tg ranging from 0° C. to 45° C., grafted with chains derived from acrylic and/or methacrylic monomers and having, in contrast, a Tg ranging from 50° C. to 200° C.

Preferably, the adhesivity of the adhesive layer is such that the adhesive article cannot be removed by manual peeling after application to the surface of a keratin material for 8 hours, more preferably 12 hours, and more preferably 24 hours.

The adhesive layer preferably has a thickness of from 1 micron to 100 microns, in particular from 1 micron to 50 microns, and most preferably from 1 micron to 25 microns.

According to preferred embodiments, the adhesive layer leads to a work of debonding (tack) greater than 0.5 J/m$^2$. This is particularly preferred when the adhesive layer is substantially free of solvent.

Polymeric or Functional Layer

According to the present invention, adhesive articles comprising a polymeric or functional layer are provided. In accordance with the present invention, the polymeric layer can be a single polymeric layer. However, the polymeric layer can also be a combination of two or more polymeric sub-layers which, combined, form the polymeric layer.

According to preferred embodiments, the polymeric layer comprises a first layer and a second layer adjacent to said first layer. If desired, the second layer may be substantially transparent. According to preferred embodiments, the thickness of the second layer is preferably less than 20 µm, and more preferably less than 10 µm, the ratio between the thickness of the first layer and the thickness of the second layer preferably ranging from 3 to 50, preferably from 4 to 25, and more preferably from 5 to 20, including all ranges and subranges therebetween.

In accordance with the present invention, the polymeric layer (or sub-layer(s)) comprises at least one film forming polymer. According to preferred embodiments, the polymeric layer (or sub-layer) optionally further comprises at least one co-film forming agent and/or at least one film modifying agent.

According to particularly preferred embodiments, the adhesive article comprising the polymeric layer has a Persoz hardness less than 50 seconds, preferably less than 40 seconds, more preferably less than 35 seconds, and most preferably less than 30 seconds, and/or a resistance to abrasion corresponding to a weight loss lower than 50 mg, preferably lower than 40 mg, more preferably lower than 30 mg, and most preferably lower than 20 mg, the polymeric arrangement being configured so that, when the article is also substantially free of solvent, the elongation at break of the article is greater than 30%, preferably greater than 40%, more preferably greater than 50%, and most preferably greater than 60%.

According to preferred embodiments of the present invention, the adhesive layer is directly in contact with the polymeric layer. Accordingly, it is preferred that the materials in the adhesive layer and the materials in the polymeric layer are compatible by virtue of their chemical nature. For example, the solvent for the adhesive material can be capable of leading to an increase in the mass of the cross-linked film placed in contact therewith such as, for example, by at least 10% by weight relative to the initial weight of the crosslinked film. Such an increase can be reflected more specifically by a gain in mass of the film.

Film Forming Polymer

According to the present invention, the polymeric layer comprises at least one film forming agent. In accordance with the present invention, any suitable film forming agent can be used. "Film former" or "film forming agent" as used herein means a polymer or resin that leaves a film on the substrate to which it is applied, for example, after a solvent accompanying the film former has evaporated, absorbed into and/or dissipated on the substrate.

According to preferred embodiments of the present invention, the film forming agent is a solid polymer having a molecular weight greater than its entanglement spacing. For purposes of the present invention, "entanglement spacing" can be calculated using the G' modulus in the plateau zone. As explained in Extract of "Viscoelastic Properties of Polymers" Second Edition 1970—John D. Ferry—John Wiley & Sons, Inc., page 403-404:

"In the conceptual scheme of entanglement coupling, the most important parameter is the average molecular weight between coupling loci, $M_e$, or the average number of chain atoms, $jP_e = jM_e/M_0$, where j is the number of chain atoms per monomer unit and $M_0$ the monomer molecular weight; " . . . " There are several methods for estimating its values.

If G' were absolutely independent of frequency in the plateau zone " . . . " its value here, which may be called $G_{eN}^0$, the pseudo-equilibrium modulus of the entanglement network, could be related " . . . " to the density of entanglement network strands $v_e$:

$$G_{eN}^0 = g_N v_e RT = g_N \rho RT/M_e = 1/J_{eN}^0$$

where $g_N$ is a numerical factor not far from unity (not necessary the same as g in the earlier equation) and ρ is the density. The value of $G_{eN}^0$ could similarly be obtained from the plateau zone of the relaxation modulus; or its reciprocal, $J_{eN}^0$ " . . . ", from the plateau of the creep compliance or the dynamic storage compliance.

Many values estimated in this manner have been given in the literature." Examples are given in Table 1 below.

| Polymer | Temp. ° C. | log $J_{eN}^0$ | $M_e$ | j | $M_e$ | $jP_e$ | Ref. |
|---|---|---|---|---|---|---|---|
| Methacrylate Polymers | | | | | | | |
| Methyl (atactic) | 110 | −6.79 | 5,900 | 2 | 100 | 59 | 15 |
| 2-Ethyl Butyl | 100 | −6.16 | 21,400 | 2 | 170 | 130 | 16 |
| n-Hexyl | 100 | −5.94 | 33,900 | 2 | 170 | 200 | 17 |
| n-Octyl | 100 | −5.52 | 87,000 | 2 | 198 | 440 | 18 |

-continued

| Polymer | Temp. °C. | log J$_{eN}$⁰ | M$_e$ | j | M$_e$ | jP$_e$ | Ref. |
|---|---|---|---|---|---|---|---|
| Rubbers | | | | | | | |
| Hevca rubber | 25 | −6.59 | 5,750 | 4 | 68 | 340 | 1 |
| 1,4-polybutadiene[a] | 25 | −7.06 | 1,900 | 4 | 54 | 140 | 2 |
| 1,4-polybutadiene, cis[b] | 25 | −6.88 | 2,950 | 4 | 54 | 220 | 19 |
| 1,2-polybutadiene | 25 | −6.79 | 3,550 | 2 | 54 | 130 | 1 |
| Styrene-butadiene copolymer[c] | 25 | −6.89 | 3,000 | 4 | 65.5 | 180 | 20 |
| Butyl rubber[d] | 25 | −6.46 | 8,500 | 2 | 56 | 300 | 19 |
| Ethylene-propylene copolymer[e] | 25 | −7.10 | 1,660 | 2 | 34.3 | 100 | 21 |
| General | | | | | | | |
| Polyisobutylene | 25 | −6.40 | 8,900 | 2 | 56 | 320 | 22 |
| Polydimethyl siloxane[f] | 25 | −6.47 | 8,100 | 2 | 74 | 220 | 23 |
| Polystyrene[g] | 160 | −6.30 | 18,100 | 2 | 104 | 350 | 3 |

Examples of chemistries from which suitable polymers or copolymers can be chosen include but are not limited to, polyolefins (polyethylene, polypropylene, polyisobutylene, etc.), polyvinyl chloride, polyvinyl acetate and its derivatives, styrenics, polyacrylics, polyesters, polyamides, polyimides, polyoxyalkylenes, fluorated polymers, cellulosics, polymers with aromatic skeletons, polycarbonates, aromatic polysulfones, polyphenylene sulfide (PPS), polyphenylene ether, polyetherimides, aromatics polyamides, polyamide-imides, polyarylethercetones, polyurethanes, silicones, phenolic polymers, formophenolic polymers, epoxies, and mixtures thereof.

According to particularly preferred embodiments, the polymeric layer comprises at least one film forming agent which is capable of being crosslinked. According to these embodiments, any means of crosslinking is acceptable such as, for example, chemically crosslinking, ionic crosslinking (complexation), and physical crosslinking (with H-Bond and/or phase segregation). Preferably, such polymer has at least one Tg (glass transition temperature) below ambient temperature. Suitable examples of such polymers include, but are not limited to:

Styrenics: Including for instance physically crosslinked Styrene-Isoprene-Styrene, Styrene-Butadiene-Styrene, Styrene-Ethylene/Butylene-Styrene, and Styrene-Ethylene/Propylene-Styrene block copolymers. Commercial grades of these chemistries are available under the trade name Kraton (for example, Kraton G and Kraton D product ranges). Also included, for instance, are physically crosslinked Styrene-Butadiene-Methylmethacrylate block copolymers available from Arkema in the Nanostrength product range;

Polyacrylics: Including for instance physically cross-linked Methylmethacrylate-Butylacrylate-Methylmethacrylate block copolymers available at Arkema in the Nanostrength product range. Also included, for instance, are UV-crosslinking Acrylic/Styrene water dispersions such as Acronal DS 6252 from BASF;

Silicones: Including for instance chemically crosslinked silicone rubber Elastosil grades from Wacker (for example, Elastosil N2010) and acrylic/silicone copolymers; and Polycondensates (including polyurethanes, acrylic polyurethanes, silicone polyurethane, polyureas, polyurea polyurethanes, polyester polyurethanes, polyether polyurethanes, polyesters, polyamides, polyester-amides, epoxies) such as, for example, physically crosslinked Polydimethylsiloxane-Urea copolymers from the Geniomer product range from Wacker.

According to other particularly preferred embodiments of the present invention, the film forming polymer has at least one Tg greater than ambient temperature and a molecular weight greater than the entanglement weight of the polymer. Suitable examples of such polymers include, but are not limited to:

(Meth)acrylic acid ester and/or amide homo and copolymers, in particular polymers resulting from the polymerization or copolymerization of methyl, ethyl, propyl, butyl, isobutyl, tert-butyl, pentyl, hexyl, cyclohexyl, 2 ethylhexyl, heptyl, octyl, isobornyl, norbornyl or adamantyl acrylates and/or methacrylates, or the corresponding (meth)acrylamides. These polymers preferably comprise up to 20% of a polar comonomer such as, for example, (meth)acrylic acid, (meth)acrylamide, hydroxyethyl(meth)acrylate, 2 hydroxypropyl(meth)acrylate, (meth)acrylonitrile, and mixtures thereof. They may also result from copolymerization of at least one of the monomers mentioned with styrene or a substituted styrene;

Vinyl ester or amide homo and copolymers, in particular homo and copolymers resulting from the polymerization of vinyl acetate, vinyl propionate or vinyl versatate, with or without the presence of a polar comonomer such as crotonic acid, allyloxyacetic acid, maleic anhydride (or acid), itaconic anhydride (or acid), vinylacetamide and vinylformamide. Similarly, such polymers may result from the copolymerization of at least one of the monomers mentioned with styrene or a substituted styrene. Thus, suitable vinyl polymers can result from the homopolymerization or from the copolymerization of monomers chosen from vinyl esters, styrene or butadiene. As an example of vinyl esters, mention may be made of vinyl acetate, vinyl neodecanoate, vinyl pivalate, vinyl benzoate and vinyl t-butyl benzoate;

Celluloses and cellulose derivatives, for instance cellulose esters such as cellulose acetates, cellulose propionates, cellulose butyrates, cellulose acetopropionates and cellulose acetobutyrates; and Polycondensates, preferably chosen from the following polymers and copolymers: polyurethanes, acrylic polyurethanes, polyureas, polyurea polyurethanes, polyester polyurethanes, polyether polyurethanes, polyesters, polyester-amides, fatty chain polyesters, epoxies.

Polyesters include those obtained, in a known manner, by polycondensation of aliphatic or aromatic diacids with aliphatic or aromatic diols or polyols. As aliphatic diacids, use may be made of succinic acid, glutaric acid, adipic acid, pimelic acid, suberic acid or sebacic acid. As aromatic diacids, use may be made of terephthalic acid or isophthalic acid, alternatively a derivative such as phthalic anhydride. As aliphatic diols, use may be made of ethylene glycol, propylene glycol, diethylene glycol, neopentyl glycol. cyclohexane-dimethanol, or 4,4'-(1-methylpropylidene)bis-phenol. As polyols, use may be made of glycerol, pentaerythritol, sorbitol or trimethylolpropane.

According to one embodiment of the present invention, the film-forming agent is a film-forming linear block ethylenic polymer, which preferably comprises at least a first block and at least a second block having different glass transition temperatures (Tg), said first and second blocks being connected to one another via an intermediate block comprising at least one monomer that constitutes the first block and at least one monomer that constitutes the second block. Advantageously, the first and second blocks of the block polymer are incompatible with one another. Such polymers are described, for example, in documents EP 1411069 or WO 04/028488, the entire disclosures of which are hereby incorporated by reference.

According to other embodiments, aqueous dispersions of particles, aqueous dispersions of film-forming polymers, or latex can be used in the polymeric layer For example, the polymeric layer can result from the evaporation of the aqueous phase of an aqueous dispersion of particles of film-forming polymer(s). Suitable film-forming polymers for such uses include but are not limited to synthetic polymers of the polycondensate type or of the free-radical type, polymers of natural origin, and mixtures thereof. Specific examples of suitable film forming polymers include but are not limited to, in the form of latex, polycondensates, polyurethanes, polyurethane-acrylics, polyurethane-polyvinylpyrrolidones, polyester-polyurethanes, polyether-polyurethanes, polyureas, polyurea-polyurethanes, polyesters, polyester amides, fatty chain polyesters, polyamides, epoxy ester resins, and mixtures thereof.

The polymers of free-radical type may in particular be acrylic and/or vinyl polymers or copolymers. Anionic free-radical polymers are preferred. As a monomer bearing an anionic group that can be used during the free-radical polymerization, mention may be made of acrylic acid, methacrylic acid, crotonic acid, maleic anhydride, or 2 acrylamido-2-methylpropanesulphonic acid. The acrylic polymers can result from the copolymerization of monomers chosen from esters and/or amides of acrylic acid or of methacrylic acid. As an example of monomers of ester type, mention may be made of methyl methacrylate, ethyl methacrylate, butyl methacrylate, isobutyl methacrylate, 2 ethylhexyl methacrylate and lauryl methacrylate. As an example of monomers of amide type, mention may be made of N t-butylacrylamide and of N t-octylacrylamide.

Mention may also be made of polymers resulting from the free-radical polymerization of one or more free-radical monomers within and/or partially at the surface of pre-existing particles of at least one polymer chosen from the group consisting of polyurethanes, polyureas, polyesters, polyester amides and/or alkyds. These polymers are generally called hybrid polymers.

The film forming polymer is present in the polymeric layer in an amount ranging from about 1% to about 100%, preferably from about 25% to about 100%, and preferably from about 50% to about 100% by weight with respect to the total weight of the polymeric layer including all ranges and subranges therebetween.

Film Modifying Agent

According to preferred embodiments of the present invention, the polymeric layer can further optionally comprise at least one film modifying agent. In accordance with the present invention, a "film modifying agent" is an agent which modifies any physical property of the film such as, for example, tensile strength, elongation, brittleness and/or flexibility.

Suitable examples of film modifying agents include, but are not limited to, plasticizers, coalescence agents, tackifiers, humectants and antimicrobial agents.

Suitable film modifying agents include, for example, glycols and their derivatives such as diethylene glycol ethyl ether, diethylene glycol methyl ether, diethylene glycol butyl ether, diethylene glycol hexyl ether, ethylene glycol ethyl ether, ethylene glycol butyl ether or ethylene glycol hexyl ether; glycol esters, derivatives of propylene glycol, and in particular propylene glycol phenyl ether, propylene glycol diacetate, dipropylene glycol butyl ether, tripropylene glycol butyl ether, propylene glycol methyl ether, dipropylene glycol ethyl ether, tripropylene glycol methyl ether and diethylene glycol methyl ether, propylene glycol butyl ether, esters of acids, in particular carboxylic acids, such as citrates, in particular triethyl citrate, tributyl citrate, triethyl acetylcitrate, tributyl acetylcitrate, 2 triethylhexyl acetylcitrate; phthalates, in particular diethyl phthalate, dibutyl phthalate, dioctyl phthalate, dipentyl phthalate, dimethoxyethyl phthalate; phosphates, in particular tricresyl phosphate, tributyl phosphate, triphenyl phosphate, tributoxyethyl phosphate; tartrates, in particular dibutyl tartrate; adipates; carbonates; sebacates; benzyl benzoate, butyl acetylricinoleate, glyceryl acetylricinoleate, butyl glycolate, camphor, glyceryl triacetate, N ethyl-o,p-toluenesulfonamide, oxyethylenated derivatives such as oxyethylenated oils, in particular plant oils such as castor oil; silicone oils, and mixtures thereof.

If present, the film modifying agent is present in the polymeric layer in an amount ranging from about 0.1% to about 99%, preferably from about 1% to about 75%, and preferably from about 10% to about 50% by weight with respect to the total weight of the polymeric layer including all ranges and subranges therebetween, and the film modifying agent and the film forming agent are present in the polymeric layer in a weight ratio of about 10:1 to about 1:100, preferably of about 2:1 to about 1:10, preferably from about 1:1 to about 1:5, including all ranges and subranges therebetween.

Co-Film Forming Polymer

According to preferred embodiments of the present invention, the polymeric layer can further optionally comprise at least one co-film forming polymer. Preferably, the co-film forming polymer has a molecular weight (Mw) below 20000 g/mol.

Preferred examples of co-film forming polymers include polycondensates such as those discussed above, particularly in combination with cellulose ester film forming agents. Specific examples of such co-film forming polymers include polyesters (in particular fatty chain polyesters, and more particularly copolymers having the CTFA name: "phthalic anhydride/glycerol/glycidyl decanoate copolymer" and "adipic acid, neopentyl glycol/trimellitic anhydride copolymer"), alkyds, tosylamide/formaldehyde condensates, polyurethanes and polyurea-urethanes, acrylic resins, silicone resins (non-volatile or partially volatile).

If present, the co-film forming polymer is present in the polymeric layer in an amount ranging from about 1% to about 99%, preferably from about 10% to about 90%, and preferably from about 25% to about 75% by weight with respect to the total weight of the polymeric layer including all ranges and subranges therebetween, and the co-film forming polymer and the film forming agent are present in the polymeric layer in a weight ratio of about 100:1 to about 1:100, preferably of about 10:1 to about 1:10, preferably from about 3:1 to about 1:3, including all ranges and subranges therebetween.

Protective or Removable Layer

According to preferred embodiments of the present invention, the adhesive article can further optionally comprise at least one protective or removable layer or substrate. The protective or removable layer can be adjacent to the adhesive layer, the polymeric layer, or both. If adjacent to the adhesive layer, the protective or removable layer allows the adhesive layer to maintain adhesivity until its removal, and it protects the adhesive layer as well. If adjacent to the polymeric layer, the protective or removable layer protects the polymeric layer until its removal.

Suitable protective or removable layers include, but are not limited to, removable liners such as are known in the transdermal patch art such as, for example, a low energy polymeric film like polyethylene, PTFE or paper, optionally coated with a release polymer like a silicone polymer.

According to particularly preferred embodiments of the present invention, the adhesive article of the present invention presents a thermal resistance leading to a weight loss at 250° C. lower than 30%, preferably lower than 20%, and more preferably lower than 10%.

Also according to particularly preferred embodiments, the adhesive article of the present invention comprises:

I) an adhesive layer having a first surface and a second surface opposed to said first surface;

II) a polymeric arrangement that may be one or more layers comprising at least one film forming polymer, and having a first surface in contact with said first surface of the adhesive layer and a second surface opposed to said first surface, the second surface of the polymeric layered arrangement having, when the article is substantially free of solvent, a Persoz hardness less than 50 seconds, preferably less than 40 seconds, more preferably less than 35 seconds, and highly preferably less than 30 seconds, and a resistance to abrasion corresponding to a weight loss lower than 50 mg, preferably lower than 40 mg, more preferably lower than 30 mg, and highly preferably lower than 20 mg, the polymeric arrangement being configured so that, when the article is also substantially free of solvent, the elongation at break of the article is greater than 30%, preferably greater than 40%, more preferably greater than 50%, and highly preferably greater than 60%, the polymeric arrangement comprising:

a) a first layer having said first surface and comprising i) a film forming polymer as described above; and ii) an auxiliary film modifying agent as described above; and b) a second layer adjacent said first layer and having said second surface of the polymeric arrangement, said second layer comprising a film forming polymer chosen from:

1) (Meth)acrylic acid ester and/or amide homo and copolymers, in particular polymers resulting from the polymerization or copolymerization of methyl, ethyl, propyl, butyl, isobutyl, tert-butyl, pentyl, hexyl, cyclohexyl, 2 ethylhexyl, heptyl, octyl, isobornyl, norbornyl or adamantyl acrylates and/or methacrylates, or the corresponding (meth)acrylamides. These polymers preferably comprise from 0 to 20% of a polar comonomer such as (meth)acrylic acid, (meth) acrylamide, hydroxyethyl(meth)acrylate, 2 hydroxypropyl (meth)acrylate, and (meth)acrylonitrile. They may also result from copolymerization with styrene or a substituted styrene;

2) Vinyl ester or amide homo and copolymers, in particular homo and copolymers resulting from the polymerization of vinyl acetate, vinyl propionate or vinyl versatate, with or without the presence of a polar comonomer such as crotonic acid, allyloxyacetic acid, maleic anhydride (or acid), itaconic anhydride (or acid), vinylacetamide and vinylformamide. Similarly, they may result from the copolymerization of at least one of the monomers mentioned with styrene or a substituted styrene;

3) Celluloses and cellulose derivatives, for instance nitrocelluloses and/or cellulose esters such as cellulose acetates, cellulose propionates, cellulose butyrates, cellulose acetopropionates and cellulose acetobutyrates;

4) Polycondensates, preferably chosen from the following polymers and copolymers: polyurethanes, acrylic polyurethanes, polyureas, polyurea polyurethanes, polyester polyurethanes, polyether polyurethanes, polyesters, polyesteramides, fatty chain polyesters, epoxies.

Polyesters include those obtained, in a known manner, by polycondensation of aliphatic or aromatic diacids with aliphatic or aromatic diols or polyols. As aliphatic diacids, use may be made of succinic acid, glutaric acid, adipic acid, pimelic acid, suberic acid or sebacic acid. As aromatic diacids, use may be made of terephthalic acid or isophthalic acid, alternatively a derivative such as phthalic anhydride. As aliphatic diols, use may be made of ethylene glycol, propylene glycol, diethylene glycol, neopentyl glycol. cyclohexane dimethanol, or 4,4'-(1-methylpropylidene)bisphenol. As polyols, use may be made of glycerol, pentaerythritol, sorbitol or trimethylolpropane.

According to one embodiment of the invention, the film-forming polymer is a film-forming linear block ethylenic polymer, which preferably comprises at least a first block and at least a second block having different glass transition temperatures (Tg), said first and second blocks being connected to one another via an intermediate block comprising at least one monomer that constitutes the first block and at least one monomer that constitutes the second block. Advantageously, the first and second blocks of the block polymer are incompatible with one another. Such polymers are described, for example, in documents EP 1411069 or WO 04/028488, the entire contents of which are hereby incorporated by reference.

According to another embodiment of the invention, the polymeric layer derives from the evaporation of the aqueous phase of an aqueous dispersion of particles of film-forming polymer(s). In this case, the film-forming polymer can be chosen from aqueous dispersions of particles of film-forming polymers or alternatively latex and, in this case, the composition according to the invention comprises at least one aqueous phase.

The aqueous dispersion comprising one or more film-forming polymers can be prepared by those skilled in the art on the basis of their general knowledge, in particular by emulsion polymerization or by dispersion of the pre-formed polymer. Among the film-forming polymers of this type that can be used in the composition according to the present invention, mention may be made of synthetic polymers, of the polycondensate type or of the free-radical type, polymers of natural origin, and blends thereof. Specific examples of such materials include, but are not limited to, polymers (homo and copolymers) that are mentioned above, and more particularly the polymers of classes 1-3 above.

For example, among the polycondensates, mention may thus be made of anionic, cationic, non-ionic or amphoteric polyurethanes, polyurethane-acrylics, polyurethane-polyvinylpyrrolidones, polyester-polyurethanes, polyether-polyurethanes, polyureas, polyurea-polyurethanes, and blends thereof.

Mention may also be made of polyesters, polyester amides, fatty chain polyesters, polyamides and epoxy ester resins. Such polyesters can be obtained, in a known manner, by polycondensation of aliphatic or aromatic diacids with aliphatic or aromatic diols or polyols. As aliphatic diacids, use may be made of succinic acid, glutaric acid, adipic acid, pimelic acid, suberic acid or sebacic acid. As aromatic diacids, use may be made of terephthalic acid or isophthalic acid, alternatively a derivative such as phthalic anhydride. As aliphatic diols, use may be made of ethylene glycol, propylene glycol, diethylene glycol, neopentyl glycol. cyclohexane dimethanol, or 4,4'-(1-methylpropylidene) bisphenol. As polyols, use may be made of glycerol, pentaerythritol, sorbitol or trimethylolpropane.

The polymers of free-radical type may in particular be acrylic and/or vinyl polymers or copolymers. Anionic free-radical polymers are preferably used. As a monomer bearing an anionic group that can be used during the free-radical polymerization, mention may be made of acrylic acid, methacrylic acid, crotonic acid, maleic anhydride, or 2 acrylamido-2-methylpropanesulphonic acid. The acrylic polymers can result from the copolymerization of monomers chosen from esters and/or amides of acrylic acid or of methacrylic acid. As an example of monomers of ester type, mention may be made of methyl methacrylate, ethyl methacrylate, butyl methacrylate, isobutyl methacrylate, 2 ethylhexyl methacrylate and lauryl methacrylate. As an example of monomers of amide type, mention may be made of N t-butylacrylamide and of N t-octylacrylamide. The vinyl polymers can result from the homopolymerization or from the copolymerization of monomers chosen from vinyl esters, styrene or butadiene. As an example of vinyl esters, mention may be made of vinyl acetate, vinyl neodecanoate, vinyl pivalate, vinyl benzoate and vinyl t-butyl benzoate. Acrylic/silicone copolymers can also be used.

Mention may also be made of polymers resulting from the free-radical polymerization of one or more free-radical monomers within and/or partially at the surface of pre-existing particles of at least one polymer chosen from the group consisting of polyurethanes, polyureas, polyesters, polyester amides and/or alkyds. These polymers are generally called hybrid polymers.

Colorants and Active Agents

According to preferred embodiments of the present invention, the adhesive articles further comprise a colorant and/or active agent in at least one of the layers of the article. Preferably, the polymeric layer comprises colorant and/or active agent. However, the adhesive layer may contain colorant and/or active agent in addition to, or instead of, the polymeric layer. Colorants such as pigments or dyes can provide aesthetic benefits to keratin materials to which the articles have been applied. Active agents can provide cosmetic or pharmacological benefits to keratin materials to which the articles have been applied.

Thus, for example, the compositions can include hardening or strengthening agents for keratinous materials, actives promoting nail growth such as methylsulphonylmethane and/or actives for treating various disorders localized at the nails, for example antimycotics or antimicrobials.

Suitable colorants include pigments, dyes and nacres conventionally used in cosmetic compositions, including both organic or inorganic colorants, conventionally used in cosmetic compositions. Pigments include white or colored particles, mineral or organic, intended for coloring and/or opacifying the resultant product. Preferably, pigments or nacres, if present, are present in an amount ranging from 0.01 to 30 wt. %, more preferably from 0.01 to 20 wt. %, and most preferably from 0.02 to 10 wt. %, relative to the total weight of the adhesive article, including all ranges and subranges therebetween.

Specific examples of suitable pigments include, but are not limited to, the oxides of titanium, of zirconium or of cerium, as well as the oxides of zinc, of iron or of chromium, ferric blue, manganese violet, ultramarine and chromium hydroxide.

The pigment can also have a structure which can be, for example, of the sericite/brown iron oxide/titanium dioxide/silica type. Such a pigment is marketed, for example, under the reference COVERLEAF NS or JS by the company CHEMICALS AND CATALYSTS and has a contrast ratio close to 30.

The pigment can also have a structure which can be, for example, silica microspheres containing iron oxide. An example of a pigment having this structure is marketed by the company MIYOSHI under the reference PC BALL PC-LL-100 P.

Suitable organic pigments that can be used in accordance with the present invention include carbon black, pigments of the D & C type, lakes based on carmine, barium, strontium, calcium, aluminium or diketo-pyrrolopyrrole (DPP) described in documents EP-A-542669, EP-A-787730, EP-A-787731 and WO-A-96/08537, the entire contents of which are hereby incorporated by reference.

"Nacres" are colored particles of any shape, iridescent or not, notably produced in the shell of certain molluscs or alternatively synthesized, and which display a color effect by optical interference. Suitable nacres can be selected from the nacreous pigments such as titanium mica coated with an iron oxide, mica coated with bismuth oxychloride, titanium mica coated with chromium oxide, titanium mica coated with an organic colorant as well as nacreous pigments based on bismuth oxychloride, and mica particles, the surface of which is coated with at least two successive layers of metal oxides and/or organic colorants. Among the nacres that are available commercially, TIMICA, FLAMENCO and DUOCHROME (mica-based) marketed by the company ENGELHARD, the TIMIRON nacres marketed by the company MERCK, the PRESTIGE mica-based nacres marketed by the company ECKART and the SUNSHINE nacres based on synthetic mica, marketed by the company SUN CHEMICAL are suitable.

Suitable nacres can possess a yellow, pink, red, bronze, orange, brown, golden and/or coppery color or sheen. Such suitable nacres include the gold-colored nacres notably marketed by the company ENGELHARD under the name of Brillant gold 212G (Timica), Gold 222C (Cloisonne), Sparkle gold (Timica), Gold 4504 (Chromalite) and Monarch gold 233X (Cloisonne); the bronze nacres notably marketed by the company MERCK under the designation Bronze fine (17384) (Colorona) and Bronze (17353) (Colorona) and by the company ENGELHARD under the designation Super bronze (Cloisonne); the orange nacres notably marketed by the company ENGELHARD under the designation Orange 363C (Cloisonne) and Orange MCR 101 (Cosmica) and by the company MERCK under the designation Passion orange (Colorona) and Matte orange (17449) (Microna); the brown nacres notably marketed by the company ENGELHARD under the designation Nu-antique copper 340XB (Cloisonne) and Brown CL4509 (Chromalite); the nacres with a copper sheen notably marketed by the company ENGELHARD under the designation Copper 340A (Timica); the nacres with a red sheen notably marketed by the company MERCK under the designation Sienna fine (17386) (Colorona); the nacres with a yellow sheen notably marketed by the company ENGELHARD under the designation Yellow (4502) (Chromalite); the red nacres with a golden sheen notably marketed by the company ENGELHARD under the designation Sunstone G012 (Gemtone); the pink nacres notably marketed by the company ENGELHARD under the designation Tan opal G005 (Gemtone); the black nacres with a golden sheen notably marketed by the company ENGELHARD under the designation Nu antique bronze 240 AB (Timica), the blue nacres notably marketed by the company MERCK under the designation Matte blue (17433) (Microna), the white nacres with a silvery sheen notably marketed by the company MERCK under the designation Xirona Silver and the orange pink golden green nacres notably marketed by the company MERCK under the designation Indian summer (Xirona) and mixtures thereof.

According to preferred embodiments, one or more layers of the adhesive article according to the invention can contain water-soluble or fat-soluble colorants (dyes). If present, the dyes are present in an amount preferably ranging from 0.01 to 10 wt. %, and more preferably in the range from 0.01 to 5 wt. % relative to the total weight of the article. Suitable examples of fat-soluble colorants include, for example, Sudan Red, DC Red 17, DC Green 6, [beta]-carotene, soya oil, Sudan Brown, DC Yellow 11, DC Violet 2, DC Orange 5, quinoline yellow. Suitable examples of water-soluble colorants include, for example, beetroot juice and methylene blue.

"Special effect materials" may also be included in the articles of the present invention, if desired. Such materials can possess specific optical effects which differ from conventional coloring. Preferably, if present, such special effect materials are present in the polymeric layer. Also preferably, such materials are present in an amount sufficient to produce an optical effect that is perceptible with the naked eye. For example, such materials are preferably present in an amount ranging from 0.01 to 20%, and more preferably from 0.1 to 10% by weight relative to the total weight of the article.

Suitable special effect materials include, but are not limited to, those which provide goniochromatic, metallic, mirror, soft-focus, rainbow, thermochromic and/or photochromic effects. For example, such materials include particles with a metallic sheen, goniochromatic colorants, diffracting pigments, thermochromic and photochromic agents, optical brighteners, as well as fibres, notably interference fibres. Of course, these various materials can be combined so as to produce two effects simultaneously.

"Particles with a metallic sheen" denotes particles whose nature, size, structure and surface condition permit them to reflect incident light notably in a non-iridescent manner. Particles having a substantially flat external surface are also suitable, as they can more easily give rise, if permitted by their size, their structure and their surface condition, to intense specular reflection, which can then be described as a mirror effect. The particles with a metallic sheen that can be used in the invention, can for example reflect all the components of visible light without significantly absorbing one or more wavelengths. The spectral reflectance of these particles can for example be greater than 70% in the range 400-700 nm, and preferably at least 80%, or even 90% or 95%. These particles generally have a thickness less than or equal to 1 μm, notably less than or equal to 0.7 μm, and in particular less than or equal to 0.5 μm. The total proportion of particles with a metallic sheen is notably less than or equal to 30 wt. % and in particular less than or equal to 10 wt. % relative to the total weight of the laminate. The particles with a metallic sheen that can be used in the invention are in particular selected from: particles of at least one metal and/or of at least one metallic derivative, particles having a substrate, organic or mineral, monomaterial or multimaterial, coated at least partially with at least one layer with a metallic sheen, comprising at least one metal and/or at least one metallic derivative, and mixtures of said particles. Among the metals that can be present in said particles, we may mention for example Ag, Au, Cu, Al, Ni, Sn, Mg, Cr, Mo, Ti, Zr, Pt, Va, Rb, W, Zn, Ge, Te, Se and mixtures or alloys thereof. Ag, Au, Cu, Al, Zn, Ni, Mo, Cr, and mixtures or alloys thereof (for example bronzes and brasses) are the preferred metals.

"Metallic derivatives" denotes compounds derived from metals, notably oxides, fluorides, chlorides and sulphides. Among the metallic derivatives that can be present in said particles, we may notably mention the metal oxides, for example the oxides of titanium, notably $TiO_2$, of iron, notably $Fe_2O_3$, of tin, of chromium, barium sulphate and the following compounds: $MgF_2$, $CrF_3$, $ZnS$, $ZnSe$, $SiO_2$, $Al_2O_3$, $MgO$, $Y_2O_3$, $SeO_3$, $SiO$, $HfO_2$, $ZrO_2$, $CeO_2$, $Nb_2O_5$, $Ta_2O_5$, $MoS_2$ and mixtures or alloys thereof.

According to preferred embodiments, the particles with a metallic sheen can be composed of at least one metal as defined previously, of at least one metallic derivative as defined previously, or of one of the mixtures thereof. These particles can be at least partially coated with a layer of another material, for example of transparent material such as notably rosin, silica, stearates, polysiloxanes, polyester resins, epoxy resins, polyurethane resins and acrylic resins. As examples of these particles, we may mention aluminium particles, such as those marketed under the designations STARBRITE 1200 EAC® by the company SIBERLINE and METALURE® by the company ECKART. Mention may also be made of metallic powders of copper or of alloy mixtures such as references 2844 marketed by the company RADIUM BRONZE, the metallic pigments such as aluminium or bronze, such as those marketed under the designations ROTOSAFE 700 by the company ECKART, the silica-coated aluminium particles marketed under the designation VISIONAIRE BRIGHT SILVER by the company ECKART and the metal alloy particles such as the silica-coated bronze powders (alloy of copper and zinc) marketed under the designation Visionaire Bright Natural Gold by the company Eckart.

According to preferred embodiments, these particles with metallic sheen can be particles having a substrate and which therefore have a multilayer, for example bilayer, structure. This substrate can be organic or mineral, natural or synthetic, monomaterial or multimaterial, filled or hollow. When the substrate is synthetic, it can be produced with a form that promotes the formation of a reflective surface after coating, notably after deposition of a layer of materials with a metallic sheen. The substrate can, for example, have a flat surface and the layer of materials with a metallic sheen can have an approximately uniform thickness. Preferably, the substrate can be selected from the metals and the metallic derivatives as mentioned previously, and also from glasses, ceramics, aluminas, silicas, silicates and notably aluminosilicates and borosilicates, synthetic mica such as fluorophlogopite, and mixtures thereof. The layer with a metallic sheen can coat the substrate completely or partially, and this layer can be at least partially covered with a layer of another material, for example a transparent material.

According to preferred embodiments, the layer with a metallic sheen coats a substrate completely, directly or indirectly (for example, at least one, metallic or nonmetallic, intermediate layer is interposed between the substrate and the layer). The metals or metallic derivatives that can be used in the reflective layer are as defined above. For example, it can be formed from at least one metal selected from silver, aluminum, chromium, nickel, molybdenum, gold, copper, tin, magnesium and mixtures thereof (alloys). Silver, chromium, nickel, molybdenum, and mixtures thereof, are used more particularly. The following may be mentioned more particularly as examples of this second type of particles: Glass particles coated with a metallic layer notably those described in documents JP-A-09188830, JP-A-10158450, JP-A-10158541, JP-A-07258460 and JP-A-05017710. As examples of these particles with a glass substrate, we may mention those coated respectively with silver, gold or titanium, in the form of flakes, marketed by the company NIPPON SHEET GLASS under the designations MICROGLASS METASHINE. Particles with a glass substrate coated with silver, in the form of flakes, are sold under the designation MICROGLASS METASHINE REFSX 2025 PS by the company TOYAL. Particles with a glass substrate coated with nickel/chromium/molybdenum alloy are sold under the designation CRYSTAL STAR GF 550, GF 2525 by the same company. Those coated either with brown iron oxide, or titanium oxide, tin oxide or a mixture thereof are marketed under the designation REFLECKS® by the company ENGELHARD or under the reference METASHINE MC 2080GP by the company NIPPON SHEET GLASS. These metal-coated glass particles can be coated with silica, such as those marketed under the designation METASHINE series PSS1 or GPS1 by the company NIPPON SHEET GLASS. Spherical glass-substrate particles, metal-coated or uncoated, are notably sold under the designation PRIZMALITE MICROSPHERE by the company PRIZMALITE INDUSTRIES. Pigments from the METASHINE 1080R range marketed by the company NIPPON SHEET GLASS CO. LTD. are also suitable for the invention. These pigments, more particularly described in patent application JP 2001-11340, are flakes of C-GLASS containing 65 to 72% of $SiO_2$, coated with a layer of titanium dioxide of the rutile type ($TiO_2$). These glass flakes have an average thickness of 1 micron and an average size of 80 microns, giving a ratio of average size/average thickness of 80. They give blue, green, yellow or silvery reflections depending on the thickness of the layer of $TiO_2$. Other particles have a borosilicate substrate coated with silver, and are also called "white nacres". Particles with a metallic substrate such as aluminum, copper, bronze, in the form of flakes, are sold under the trade name STARBRITE by the company SILBERLINE and under the name VISIONAIRE by the company ECKART. Particles having a substrate of synthetic mica coated with titanium dioxide, and for example with particle size between 80 and 100 µm, with a substrate of synthetic mica (fluorophlogopite) coated with titanium dioxide representing 12% of the total weight of the particle, are sold under the designation PROMINENCE by the company NIHON KOKEN. Particles with a metallic sheen can also be selected from particles formed from a stack of at least two layers with different refractive indices. These layers can be of a polymeric or metallic nature and can notably include at least one polymeric layer. Thus, particles with a metallic effect can be particles derived from a multilayer polymer film. The materials for constituting the various layers of the multilayer structure are of course selected in such a way as to endow the particles thus formed with the desired metallic effect. Such particles are notably described in WO 99/36477, U.S. Pat. No. 6,299,979 and U.S. Pat. No. 6,387,498 and are more particularly identified in the discussion relating to goniochromatic agents.

By "diffracting pigment" we mean, in the sense of the present invention, a pigment capable of producing a color variation according to the angle of observation when lit by white light, owing to the presence of a light-diffracting structure. A diffracting pigment can comprise a diffraction grating, capable for example of diffracting an incident ray of monochromatic light in defined directions. The diffraction grating can comprise a regularly repeating unit, notably a line, the distance between two adjacent units being of the same order of magnitude as the wavelength of the incident light. When the incident light is polychromatic, the diffraction grating will separate the different spectral components of the light and produce a rainbow effect. Regarding the structure of the diffracting pigments, it may be useful to refer to the article "Pigments Exhibiting Diffractive Effects" of Alberto Argoitia and Matt Witzman, 2002, Society of Vacuum Coaters, 45th Annual Technical Conference Proceedings 2002. The diffracting pigment can be produced with units having different profiles, notably triangular, symmetrical or asymmetric, with gaps, of constant or variable width, sinusoidal. The spatial frequency of the grating and the depth of the units will be selected in relation to the degree of separation of the various orders desired. The frequency can vary for example between 500 and 3000 lines per mm. Preferably, the particles of the diffracting pigment each have a flattened shape, and notably are in the form of flakes. One and the same pigment particle can have two crossed diffraction gratings, perpendicular or otherwise. A possible structure for the diffracting pigment can comprise a layer of a reflective material, covered at least on one side with a layer of a dielectric material. The latter can endow the diffracting pigment with improved rigidity and durability. The dielectric material can be selected for example from the following materials: $MgF_2$, $SiO_2$, $Al_2O_3$, $AlF_3$, $CeF_3$, $LaF_3$, $NdF_3$, $SmF_2$, $BaF_2$, $CaF_2$, LiF and their combinations. The reflective material can be selected for example from the metals and their alloys and also from the nonmetallic reflective materials. Among the metals that can be used, we may mention Al, Ag, Cu, Au, Pt, Sn, Ti, Pd, Ni, Co, Rd, Nb, Cr and their compounds, combinations or alloys. Such a reflective material can, by itself, constitute the diffracting pigment, which will then be monolayered. As a variant, the diffracting pigment can comprise a multilayer structure having a core of a dielectric material coated with a reflective layer on at least one side, or even completely encapsulating the core. A layer of a dielectric material can also cover the reflective layer or layers. The dielectric material used is then preferably inorganic, and can be selected for example from the metal fluorides, metal oxides, metal sulfides, metal nitrides, metal carbides and their combinations. The dielectric material can be in the crystalline, semi-crystalline or amorphous state. The dielectric material, in this configuration, can for example be selected from the following materials: $MgF_2$, SiO, $SiO_2$, $Al_2O_3$, $TiO_2$, WO, AlN, BN, B4C, WC, TiC, TiN, $N_4Si_3$, ZnS, glass particles, carbon particles of the diamond type and their combinations. The diffracting pigment used can notably be selected from those described in US patent application US 2003/0031870 published on 13 Feb. 2003. A diffracting pigment can comprise for example the following structure: $MgF_2$/Al/$MgF_2$, a diffracting pigment having this structure being marketed under the designation SPECTRAFLAIR 1400 Pigment Silver by the company FLEX PRODUCTS, or SPECTRAFLAIR 1400 Pigment Silver FG. The proportion by weight of $MgF_2$ can be between 80 and 95% of the total weight of the pigment.

A goniochromatic coloring agent can exhibit a color change, also called "color flop," depending on the angle of observation, greater than that encountered with nacres. One or more goniochromatic coloring agents can be used simultaneously. The goniochromatic coloring agent can be selected such that it exhibits a relatively large color change with the angle of observation. The goniochromatic coloring agent can thus be selected so as to be able to observe, for a variation of the angle of observation between 0° and 80° under illumination at 45°, a color change ΔE of the cosmetic composition, measured in the colorimetric space CIE 1976, of at least 2. The goniochromatic coloring agent can also be selected so as to be able to observe, for illumination at 45° and variation of the angle of observation between 0° and 80°, a change Dh in the angle of tint of the cosmetic composition, in the CIE 1976 plane, of at least 30° and even at least 40° or at least 60°, and even of at least 100°. The goniochromatic coloring agent can be selected for example from multilayer interference structures and liquid crystal colorants. In the case of a multilayer structure, the latter can comprise for example at least two layers, each layer, independently or not of the other layer or layers, being made for example from at least one material selected from the group comprising the following materials: $MgF_2$, $CeF_3$, ZnS, ZnSe, Si, $SiO_2$, Ge, Te, $Fe_2O_3$, Pt, Va, $Al_2O_3$, MgO, $Y_2O_3$, $S_2O_3$, SiO, $HfO_2$, $ZrO_2$, $CeO_2$, $Nb_2O_5$, $Ta_2O_5$, $TiO_2$, Ag, Al, Au, Cu, Rb, Ti, Ta, W, Zn, $MoS_2$, cryolite, alloys, polymers and their combinations. The multilayer structure may or may not exhibit, relative to a central layer, symmetry with respect to the chemical nature of the stacked layers. Examples of symmetrical multilayer interference structures that can be used in compositions made in accordance with the invention are for example the following structures: $Al/SiO_2/Al/SiO_2/Al$, pigments having this structure being marketed by the company DUPONT DE NEMOURS; $Cr/MgF_2/Al/MgF_2/Cr$, pigments having this structure being marketed under the designation CHROMAFLAIR by the company FLEX; $MoS_2/SiO_2/Al/SiO_2/MoS_2$; $Fe_2O_3/SiO_2/Al/SiO_2/Fe_2O_3$, and $Fe_2O_3/SiO_2/Fe_2O_3/SiO_2/Fe_2O_3$, pigments having these structures being marketed under the designation SICOPEARL by the company BASF; $MoS_2/SiO_2/mica-oxide/SiO_2/MoS_2$; $Fe_2O_3/SiO_2/mica-oxide/SiO_2/Fe_2O_3$; $TiO_2/SiO_2/TiO_2$ and $TiO_2/Al_2O_3/TiO_2$; $SnO/TiO_2/SiO_2/TiO_2/SnO$; $Fe_2O_3/SiO_2/Fe_2O_3$; $SnO/mica/TiO_2/SiO_2/TiO_2/mica/SnO$, pigments having these structures being marketed under the designation XIRONA by the company MERCK (Darmstadt). As examples, these pigments can be the pigments of silica/titanium dioxide/tin oxide structure marketed under the name XIRONA MAGIC by the company MERCK, the pigments of silica/brown iron oxide structure marketed under the name XIRONA INDIAN SUMMER by the company MERCK and the pigments of silica/titanium dioxide/mica/tin oxide structure marketed under the name XIRONA CARIBBEAN BLUE by the company MERCK. We may also mention the pigments INFINITE COLORS from the company SHISEIDO. Different effects are obtained, depending on the thickness and the nature of the different layers. Thus, with the structure $Fe_2O_3/SiO_2/Al/SiO_2/Fe_2O_3$ there is transition from golden green to grey-red for $SiO_2$ layers from 320 to 350 nm; from red to golden for $SiO_2$ layers from 380 to 400 nm; from violet to green for $SiO_2$ layers from 410 to 420 nm; from copper to red for $SiO_2$ layers from 430 to 440 nm.

It is also possible to use goniochromatic coloring agents of multilayer structure comprising alternating polymeric layers. To illustrate the materials that can constitute the various layers of the multilayer structure, we may mention, as a non-limiting list: polyethylene naphthalate (PEN) and its isomers for example 2,6-, 1,4-, 1,5-, 2,7- and 2,3-PEN, polyalkylene terephthalates, polyimides, polyetherimides, atactic polystyrenes, polycarbonates, alkyl polymethacrylates and polyacrylates, syndiotactic polystyrene (sPS), syndiotactic poly-alpha-methylstyrene, syndiotactic polydichlorostyrene, copolymers and mixture of its polystyrenes, cellulose derivatives, polyalkylene polymers, fluorinated polymers, chlorinated polymers, polysulphones, polyethersulphones, polyacrylonitriles, polyamides, silicone resins, epoxy resins, polyvinyl acetate, polyether-amides, ionomeric resins, elastomers and polyurethanes. Copolymers are also suitable, for example copolymers of PEN (for example, copolymers of 2,6-, 1,4-, 1,5-, 2,7-, and/or 2,3-naphthalene dicarboxylic acid or its esters with (a) terephthalic acid or its esters; (b) isophthalic acid or its esters; (c) phthalic acid or its esters; (d) alkane glycols; (e) cycloalkane glycols (for example cyclohexane dimethanol diol); (f) alkane dicarboxylic acids; and/or (g) cycloalkane dicarboxylic acids, copolymers of polyalkylene terephthalates and styrene copolymers. In addition, each individual layer can include mixtures of two or more of the preceding polymers or copolymers. The materials for constituting the various layers of the multilayer structure are of course selected in such a way as to endow the particles thus formed with the desired optical effect. Suitable examples of pigments with a polymeric multilayer structure include those marketed by the company 3M under the designation COLOR GLITTER. The liquid crystal colorants comprise for example silicones or cellulose ethers, onto which mesomorphic groups are grafted. The liquid crystal goniochromatic particles used can be, for example, those sold by the company CHENIX as well as those marketed under the designation HELICONE® HC by the company WACKER. These agents can also be in the form of dispersed goniochromatic fibers. Such fibres can for example have a size between 50 μm and 700 μm, for example of about 300 μm. In particular, interference fibres with multilayer structure can be used. Polymer fibers with multilayer structure are notably described in documents EP-A-921217, EP-A-686858 and U.S. Pat. No. 5,472,798. The multilayer structure can comprise at least two layers, each layer, independently or not of the other layer or layers, being made from at least one synthetic polymer. The polymers present in the fibers can preferably have a refractive index in the range from 1.30 to 1.82 and preferably in the range from 1.35 to 1.75. The preferred polymers for constituting the fibers are polyesters such as polyethylene terephthalate, polyethylene naphthalate, polycarbonate; acrylic polymers such as polymethyl methacrylate; polyamides. Goniochromatic fibers with bilayer structure, polyethylene terephthalate/nylon-6, are marketed by the company TEIJIN under the designation MORPHOTEX.

According to preferred embodiments, a goniochromatic coloring agent can be combined with at least one diffracting pigment. The combination of these two materials results in a composition or a film which exhibits increased variability of color, and which therefore allows an observer to perceive a color change, or even a movement of color, in numerous conditions of observation and of illumination. The weight ratio of the diffracting pigment relative to the goniochromatic coloring agent is preferably between 85/15 and 15/85, more preferably between 80/20 and 20/80, and even more preferably between 60/40 and 40/60, for example of the order of 50/50. Such a ratio favors the production of a sustained rainbow effect and goniochromatic effect.

"Optical brighteners" are known compounds such as those described in "Fluorescent Whitening Agent, Encyclopedia of Chemical Technology, Kirk-Othmer", vol 11, p. 227-241, 4th edition, 1994, Wiley. These brighteners can be more specifically defined as compounds which essentially absorb in the UVA between 300 and 390 nm and reemit essentially between 400 and 525 nm. Suitable optical brighteners include the derivatives of stilbene, in particular the polystyrylstilbenes and the triazinestilbenes, the coumarin derivatives, in particular the hydroxycoumarins and the aminocoumarins, the oxazole, benzoxazole, imidazole, triazole, and pyrazoline derivatives, the pyrene derivatives and the porphyrin derivatives and mixtures thereof.

Suitable examples further include copolymers, for example of acrylates and/or of methacrylates, grafted with optical brightener groups as described in application FR 99 10942, the contents of which is hereby incorporated by reference. The copolymers can be used as a copolymer, or they can be used in the form of particles and/or fibres coated with said optical brightener. For example, fibers coated with optical brightener are marketed by the company LCW under the trade reference Fiberlon 54 ZO3, having a length of about 0.4 mm and a thickness of 0.5 denier, and can be used in the adhesive articles of the present invention.

Suitable examples of commercially available optical brighteners include the stilbene derivative of naphtho-triazole sold under the trade name "Tinopal GS", disodium di-styryl-4,4'biphenyl sulphonate (CTFA name: disodium distyrylbiphenyl disulphonate) sold under the trade name "Tinopal CBS-X", the cationic derivative of aminocoumarin sold under the trade name "Tinopal SWN CONC", 4,4'-bis[(4,6-dianilino-1.3,5-triazin-2-yl)amino]stilbene-2,2'-sodium disulphonate sold under the trade name "Tinopal SOP", 4,4'-bis-[(4-anilino-6-bis(2-dydroxyethyl)amino-1,3,5-triazin-2-yl)amino]stilbene-2,2'-disulphonic acid sold under the trade name "Tinopal UNPA-GX", 4,4'-bis-[anilino-6-morpholine-1,3,5-triazin-2-yl)amino]stilbene sold under the trade name "Tinopal AMS-GX", 4,4'-bis-[(4-anilino-6-(2-hydroxyethyl)methyl amino-1,3,5-triazin-2-yl)amino]stilbene-2,2'-disodium sulphonate sold under the trade name "Tinopal 5BM-GX", all from the company CIBA Specialties Chimiques, 2,5 thiophene di-yl bis(5 ter-butyl-1,3 benzoxazole) sold under the trade name "Uvitex OB" by the company CIBA, the anionic derivative of di-aminostilbene in dispersion in water sold under the trade name "Leucophor BSB liquid" by the company CLARIANT, the optical brightener lakes sold under the trade name "COVAZUR" by the company WACKHER.

According to preferred embodiments, one or more layers of the adhesive articles of the present invention can contain at least one relief effect material. According to the present invention, the relief effect material may or may not be associated with an optical effect. A relief effect material is a material which confers a relief effect (perceptible to the touch and/or naked eye) which incorporated into one of the layers. Such relief effects can confer a rough and/or hammered effect. For example, the relief material can be solid particles and/or fibres, thus providing a relief effect, or it could be a material comprising a mixture of pyrogenic silica, metallic pigment and organopolysiloxane compound to endow it with a hammered appearance such as that described in European patent application EP 1 040 813, the entire contents of which is incorporated by reference.

Including particles of approximately spherical or oval shape into the adhesive articles of the present invention can provide a soft feel to the articles. Preferably, the particles have an approximately spherical shape to allow good distribution in the article.

Preferably, the solid particles, if present, have an average size in the range from 2.5 μm to 5 mm, and preferably from 50 μm to 2 mm. The smaller the particles, the more long lasting the properties of the particles are. The use of particles is also compatible with the production of patterns.

Suitable examples of solid particles included glass, zirconium oxide, tungsten carbide, plastics such as polyurethanes, polyamides, polytetrafluoroethylene, polypropylene, metals such as steel, copper, brass, chromium; marble, onyx, jade, natural mother-of-pearl, precious stones (diamond, emerald, ruby, sapphire), amethyst, and aquamarine. Glass beads are preferably used, such as those sold under the designation "SILIBEADS®" by the company SIGMUND LINDNER; these beads have the additional advantage of also imparting a glossy and sparkling effect to the adhesive articles. The solid particles may be deformable or not, full or hollow, colorless or colored, coated or uncoated.

Suitable fibers include fibers of synthetic or natural origin, mineral or organic. A fiber is an object of length L and diameter D such that L is much greater than D, D being the diameter of the circle in which the fibre cross-section can be inscribed. Preferably, the ratio L/D (or form factor) is selected in the range from 3.5 to 2500, preferably from 5 to 500, and more preferably from 5 to 150.

Suitable materials for fibers include fibers typically used in the manufacture of textiles such as, for example, silk, cotton, wool, flax, cellulose fibres, notably extracted from wood, vegetables or algae, rayon, polyamide (Nylon®), viscose, acetate notably rayon acetate, poly-(p-phenylene-terephthalamide) (or aramid) notably Kevlar®, acrylic polymer notably polymethyl methacrylate or poly(2-hydroxyethyl methacrylate), polyolefin and notably polyethylene or polypropylene, glass, silica, carbon notably in the form of graphite, polytetrafluoroethylene (such as Teflon®), insoluble collagen, polyesters, polyvinyl chloride or vinylidene, polyvinyl alcohol, polyacrylonitrile, chitosan, polyurethane, polyethylene phthalate, fibres formed from polymer blends such as those mentioned previously, such as polyamide/polyester fibres.

According to preferred embodiments, one or more layers of the adhesive articles of the present invention can contain at least one olfactory agent such as a perfume or sweet-smelling agent.

Suitable perfumes include any known odoriferous substance such as essential oils and/or the essences. This olfactory agent can, if necessary, be incorporated into the adhesive article via a solvent-plasticizer. A "solvent-plasticizer" refers to a compound which at least partially dissolves the olfactory material and which is able to evaporate slowly.

Suitable solvent-plasticizers include, for example, glycols such as dipropylene glycol, ethyldiglycol, n-propylglycol, n-butylglycol, methyldiglycol, n-butyldiglycol; alcohols such as cyclohexanol, ethyl-2 butanol, methoxy-3 butanol, ethyl-2 hexanol, phenoxyethanol; esters, such as glycol monoacetate, ethylglycol acetate, n-butylglycol acetate, ethyldiglycol acetate, n-butyldiglycol acetate, methyl abietate, isopropyl myristate, propylene glycol diacetate, methyl ether acetate of propylene glycol; glycol ethers such as methyl ether of dipropylene glycol, butyl ether of dipropylene glycol, and mixtures thereof.

According to preferred embodiments, one or more layers of the adhesive article of the present invention can contain at least one magnetic particle. If present, such magnetic particles are preferably oriented in such a way as to yield a visible pattern as described in French patent application FR 2,882,901.

Additional Ingredients

The compositions of the present invention can also comprise any additive usually used in cosmetic or dermatologic compositions, particularly in nail cosmetic or nail care compositions. Of course, the particular ingredients added will depend upon the type of composition being prepared. Suitable examples of additional ingredients include, but are not limited to, vitamins, trace elements, emollients, sequestering agents, alkalizing or acidifying agents, wetting agents, thickeners, dispersants, anti-foaming agents, spreading agents, co-resins, preservatives, UV filters, actives, moisturizers, neutralizing agents, stabilizers, antioxidants and mixtures thereof.

The amounts of these various ingredients, if present, are preferably those conventionally used in this field and are for example from 0.01 to 30 wt. %, preferably from 0.01 to 10 wt. % relative to the total weight of the article.

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

According to preferred embodiments of the present invention, methods of producing adhesive articles are provided. In accordance with these embodiments, a first laminate comprising an adhesive layer is produced, a second laminate comprising a polymeric layer is produced, and the first and second laminates are combined to form an adhesive article comprising an adhesive layer and a polymeric layer.

According to these preferred embodiments, a first laminate comprising an adhesive layer is produced. Preferably, the first laminate is produced by coating a substrate with an adhesive material to form an adhesive layer on the substrate. Optionally, a protective or removable layer such as a plastic sheet can be applied to the adhesive layer to protect the adhesive layer until it is combined with the second laminate. The need for such an optional protective or removable layer decreases with the decrease in the amount of time between production of the first laminate and the combination of the first and second laminates to form the adhesive article. For example, if the first laminate is combined with the second laminate immediately after its production, no protective or removable layer on the first laminate may be necessary.

With specific reference to FIG. 1, a first laminate 10 is formed by coating a layer 2 of an adhesive composition onto a substrate 1. The substrate 1, as explained above, can be made of any suitable material such as polyethylene or paper coated with PTFE. After drying to possibly evaporate solvents and/or to possibly cross-link polymer(s) forming the adhesive layer, a plastic removable sheet 3 can be applied onto the adhesive layer 2. The laminate 10 is then preferably wound on a core to facilitate combination with the second laminate.

Further according to these preferred embodiments, a second laminate comprising at least one polymeric layer is produced by coating a substrate with a polymeric material to form at least one polymeric layer on the substrate. Optionally, a protective or removable layer such as a plastic sheet can be applied to the polymeric layer to protect the polymeric layer until it is combined with the first laminate. The need for such an optional protective or removable layer decreases with the decrease in the amount of time between production of the second laminate and the combination of the first and second laminates to form the adhesive article. For example, if the second laminate is combined with the first laminate immediately after its production, no protective or removable layer on the second laminate may be necessary.

With specific reference to FIG. 2, a second laminate 11 is made by coating one or more polymeric layers onto a substrate 4. The substrate 4, as explained above, can be made of any suitable material such as polyethylene or paper coated with PTFE. Preferably, at least one of the polymeric layers coated onto the substrate is colored.

As depicted in FIG. 2, a layer 5 of a colored polymeric composition onto a substrate 4. As also depicted in FIG. 2, an additional polymeric layer 6 can be coated onto the substrate 4 so that the additional polymeric layer 6 is between the substrate 4 and the colored polymeric layer 5.

Preferably, the optional polymeric layer 6, if present, is transparent. However, this additional polymeric layer is optional.

After drying to possibly evaporate solvents and/or to possibly cross-link polymer(s) forming the polymeric layer(s), a plastic removable sheet 7 can be applied onto the polymeric layer 5. The laminate 11 is then preferably wound on a core to facilitate combination with the second laminate.

Further in accordance with these preferred embodiments, the first and second laminates are combined to form an adhesive article. With specific reference to FIG. 3, the protective sheet/liner 3 of the first laminate and the protective sheet/liner 7 of the second laminate, if present, are removed. Then, both laminates 10 and 11 are brought into contact with each other via colored layer 6 and adhesive layer 2. The resulting adhesive article can then be cut 8 into various sizes and shapes, as desired.

According to preferred embodiments of the present invention, an image or design may be applied on at least one side of the polymeric layer(s). In accordance with these embodiments, such designs are preferably applied by at least one of the following processes: silk screen printing, flexographic printing, gravure printing, digital-printing (including inkjet and laser printing), digital flexographic printing, offset printing, hot stamping, or holographic lamination. In flexographic printing, for example, designs or images are engraved on rubber, polymer, or other commercially available plates affixed to a cylinder to print on the surface of at least one of the two sides of the at least one of the polymeric layers of the adhesive article. In gravure printing, designs or images are engraved on a metal cylinder to be applied to the film. The printing can be a single color or multicolor process printing and may be accomplished by various styles of designs, animations, pictures, etc.

As another example, multi-color gradation or striped nail polish film, with a design known in the industry as "vignette" can be created in or on the adhesive articles. For this type of product, two to five of nail polish colors are naturally or passively mixed and create vignette images.

As yet another example, holographic images can be created in or on the adhesive articles. For example, commercially available holographic images may be laminated on at least one of the two sides of the at least one of the polymeric layers of the adhesive article. Holographic images formed on paper or plastic film are broadly used in a variety of applications. Commercially available pre-printed holographic images (e.g, those made by Crown Roll Leaf, Inc.-Paterson N.J.) may be transferred to the surface of at least one of the two sides of the at least one of the polymeric layers of the adhesive articles by a suitable lamination process.

As yet a further example, an adhesive article having a white or other colored tip like a "French manicure" can be created. In most conventional salon French manicures, the polish application process must be performed in two or more steps. This renders the technique very difficult for the ordinary consumer looking to apply her own French manicure. However, with the current invention, the user need only apply the adhesive article to her nails in one step, and the French manicure look is achieved. The printing methods contemplated as best achieving the French manicure include but are not limited to silk screening, flexographic printing, gravure printing, digital printing (including inkjet and laser printing) or Digital Flexo, offset printing, and hot stamping.

According to other preferred embodiments of the present invention, methods of applying an adhesive article comprising colorant and/or active agent to mucosis or a keratin material are provided.

According to yet further preferred embodiments of the present invention, methods of treating, caring for, making up or enhancing the appearance of mucosis or keratin materials comprising applying adhesive articles of the present invention to the mucosis or keratin materials to treat, care for, make-up and/or enhance the appearance of the keratin materials are provided.

Both of the aforementioned methods preferably comprise applying on a mucosis or keratinous material a decorative article comprising:

I) an adhesive layer having a first surface and a second surface opposed to said first surface;

II) a polymeric arrangement that may be one or more layers comprising at least one film forming polymer, and having a first surface in contact with said first surface of the adhesive layer and a second surface opposed to said first surface, the second surface of the polymeric layered arrangement having, when the article is substantially free of solvent, a Persoz hardness less than 50 seconds, preferably less than 40 seconds, more preferably less than 35 seconds, and highly preferably less than 30 seconds, and a resistance to abrasion corresponding to a weight loss lower than 50 mg, preferably lower than 40 mg, more preferably lower than 30 mg, and highly preferably lower than 20 mg, the polymeric arrangement being configured so that, when the article is also substantially free of solvent, the elongation at break of the article is greater than 30%, preferably greater than 40%, more preferably greater than 50%, and highly preferably greater than 60%.

According to a specific embodiment of the present invention, the invention methods further comprise the step of, prior or subsequent to applying said decorative article, heating said decorative article and/or said keratinous material. Any suitable heat source can be used in accordance with this embodiment to heat up the adhesive article such as, for example, a hair dryer or a microwave. For example, the adhesive article may be submitted to an air flow whose temperature is ranging from 40° C. to 100° C., for a period of time ranging from 1 second to 10 minutes.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

Two decorative articles were prepared as described above—a first laminate containing a substrate and an adhesive layer was prepared, a second laminate containing a substrate, a transparent polymeric layer, and a colored polymeric layer was prepared (the colored polymeric layer was applied on top and after drying of the transparent polymeric layer), and then the first and second laminates were combined by contacting the adhesive layer with the colored polymeric layer. These articles are referred to as Examples 1 and 2. These articles are represented by the drawing in FIG. 4.

Both examples 1 and 2 contained a transparent topcoat (101), a colored polymeric layer (102) and an adhesive layer (103). The topcoat was a hard but thin layer, approximately 8 μm thick. The polymeric layer was thicker, approximately 75 μm thick. Finally, the adhesive layer was approximately 25 μm in thickness.

The topcoat composition was the same for both examples. It contained cellulose acetate propionate (MW 75K) (CAP 482-20 from Eastman Chemical Company) 13.5%, Co-polyester resin plasticizer (Resoflex R296 from Cambridge Industries of America, Newark, N.J.)) 1.5%, and ethyl acetate solvent 85%.

The entanglement molecular weight for the film forming polymer in the colored polymeric layer in both examples was 30,000 g/mol.

Example 1

Adhesive layer (Wet thickness: 78 microns. Dry thickness: 25 microns)—MA-83 from Adhesives Research (cross-linked acrylic polymer).

Colored polymeric layer (Wet thickness: 223 microns. Dry thickness: 71 microns)—Pigment: 3.1%, Cellulose acetate butyrate (MW 40K) (CAB 381-2 from Eastman Chemical Company): 17.3%, Co-polyester resin plasticizer (Resoflex R296 from Cambridge Industries of America, Newark, N.J.)): 11.4%, Ethyl acetate: 68.2%. The molecular weight of the polymer was 40,000 g/mol (Mn).

Topcoat layer (Wet thickness: 50 microns. Dry thickness: 7.5 microns).

The physical properties/characteristics of the Example 1 declaration article were as follows.

Glass transition temperature, Tg: −5° C. & 74° C.
Elongation at rupture: 70%
Hardness—Persoz: 25 seconds
Abrasion resistance—Taber (weight loss): 14 mg
Work of debonding: 6.75 J/m$^2$ Example 2

Adhesive layer (Wet thickness: 60.6 microns. Dry thickness: 25.4 microns)—631-72 from Adhesives Research (cross-linked acrylic polymer)

Colored polymeric layer (Wet thickness: 338 microns. Dry thickness: 76 microns)—Pigment: 2.5%, Cellulose acetate butyrate (MW 40K) (CAB 381-2 from Eastman Chemical Company): 11.4%, Co-polyester resin plasticizer (Resoflex R296 from Cambridge Industries of America, Newark, N.J.)): 8.6%, Ethyl acetate: 77.5%. The molecular weight of the polymer was 40,000 g/mol (Mn).

Topcoat layer (Wet thickness: 50.7 microns. Dry thickness: 7.6 microns).

The physical properties/characteristics of the Example 2 declaration article were as follows.

Glass transition temperature, Tg: −6° C. & 85° C.
Elongation at rupture: 70%
Hardness—Persoz: <50 seconds
Abrasion resistance—Taber (weight loss): <50 mg The following can be said about the decorative articles of both Examples 1 and 2.

The use of a soft colored polymeric layer combined with a hard but thin topcoat layer led to improved abrasion resistance as well as a high percentage elongation at break.

Also, owing to the thinness of the topcoat layer, the Persoz hardness of the total laminate remained low.

Further, the transparent topcoat layer provided good gloss properties to the article.

What is claimed is:

1. A decorative and/or cosmetic care article to be applied on a mucosis or on a keratinous material, comprising:
   i) an adhesive layer having a first surface and a second surface opposed to said first surface;
   ii) a polymeric layer comprising a first sub-layer adjacent to said adhesive layer and a second sub-layer adjacent said first sub-layer,
   wherein the first sub-layer has a first surface in contact with said first surface of the adhesive layer and the first sublayer comprises cellulose acetate butyrate,
   wherein the second sub-layer comprises cellulose acetate propionate,
   wherein the first sub-layer of the polymeric layer has, when the article is substantially free of solvent, a Persoz hardness less than 50 seconds, and a resistance to abrasion corresponding to a weight loss lower than 50 mg, the polymeric layer having, when the article is substantially free of solvent, an elongation at break of the article greater than 30%, and
   wherein the second sub-layer has a thickness of less than 20 μm.

2. The article according to claim 1, wherein the first sub-layer has a thickness and the ratio between the thickness of the first sub-layer and the thickness of the second sub-layer is from 3 to 50.

3. The article according to claim 2, wherein the ratio between the thickness of the first sub-layer and the thickness of the second sub-layer is from 4 to 25.

4. The article according to claim 2, wherein the ratio between the thickness of the first sub-layer and the thickness of the second sub-layer is from 5 to 15.

5. The article according to claim 1, wherein said second sub-layer is substantially transparent.

6. The article according to claim 1, wherein said second sub-layer is transparent.

7. The article according to claim 1, wherein the first sub-layer of the polymeric layer has, when the article is substantially free of solvent, a Persoz hardness less than 40 seconds.

8. The article according to claim 1, wherein the first sub-layer of the polymeric layer has, when the article is substantially free of solvent, a Persoz hardness less than 30 seconds.

9. The article according to claim 1, wherein said first sub-layer has a resistance to abrasion corresponding to a weight loss lower than 40 mg.

10. The article according to claim 1, wherein said first sub-layer has a resistance to abrasion corresponding to a weight loss lower than 30 mg.

11. The article according to claim 1, wherein the polymeric layer has, when the article is substantially free of solvent, an elongation at break of the article greater than 40%.

12. The article according to claim 1, wherein the polymeric layer has, when the article is substantially free of solvent, an elongation at break of the article greater than 60%.

13. The article according to claim 1, wherein the polymeric layer comprises a polymer having a molecular weight greater than its entanglement spacing.

14. The article according to claim 1, wherein the polymeric layer further comprises at least one co-film forming agent selected from the group consisting of polycondensates, polyesters, alkyds, tosylamide/formaldehyde condensates, polyurethanes, polyurea-urethanes, acrylic resins, silicone resins, and mixtures thereof.

15. A process for making-up and/or cosmetically caring for mucosis or keratinous material, comprising applying on said mucosis or keratinous material an adhesive article according to claim 1.

16. The article according to claim 1, further comprising a protective layer adjacent to the polymeric layer.

17. The article according to claim 1, wherein the polymeric layer does not contain nitrocellulose.

18. The article according to claim 16, wherein the polymeric layer does not contain nitrocellulose.

19. The article according to claim 1, wherein the second sub-layer has a thickness of less than 10 μm.

20. The article according to claim 4, wherein the second sub-layer has a thickness of less than 10 μm.

* * * * *